US010842565B2

(12) United States Patent
Anderson et al.

(10) Patent No.: US 10,842,565 B2
(45) Date of Patent: Nov. 24, 2020

(54) SYSTEMS AND METHODS FOR SELECTIVE TARGETING OF STRUCTURAL FEATURES IN TREATING SKIN CONDITIONS

(71) Applicant: THE GENERAL HOSPITAL CORPORATION, Boston, MA (US)

(72) Inventors: Richard Rox Anderson, Boston, MA (US); Yakir Levin, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 156 days.

(21) Appl. No.: 16/078,773

(22) PCT Filed: Feb. 22, 2017

(86) PCT No.: PCT/US2017/018874
§ 371 (c)(1),
(2) Date: Aug. 22, 2018

(87) PCT Pub. No.: WO2017/176380
PCT Pub. Date: Oct. 12, 2017

(65) Prior Publication Data
US 2019/0046267 A1 Feb. 14, 2019

Related U.S. Application Data

(60) Provisional application No. 62/298,227, filed on Feb. 22, 2016, provisional application No. 62/442,690, filed on Jan. 5, 2017.

(51) Int. Cl.
*A61K 49/00* (2006.01)
*A61B 18/20* (2006.01)
(Continued)

(52) U.S. Cl.
CPC .......... *A61B 18/203* (2013.01); *A61K 49/001* (2013.01); *A61K 49/0021* (2013.01);
(Continued)

(58) Field of Classification Search
CPC ........ A61B 18/203; A61B 2017/00061; A61B 2018/00458; A61B 2018/00476; A61B 2018/00577; A61B 2018/00625; A61B 2018/00642; A61B 2018/00672; A61B 2018/00678; A61B 2018/00702;
(Continued)

(56) References Cited

U.S. PATENT DOCUMENTS 5,879,346 A 3/1999 Waldman et al.
9,149,331 B2 * 10/2015 Deem ................ A61B 18/1815
(Continued)

FOREIGN PATENT DOCUMENTS

WO 2015114631 A1 8/2015

OTHER PUBLICATIONS

PCT International Search Report and Written Opinion, PCT/US17/18874, dated May 16, 2017, 16 pages.

*Primary Examiner* — George Manuel
(74) *Attorney, Agent, or Firm* — Quarles & Brady LLP (57) ABSTRACT

Systems and methods are provided for locating anatomical features in the skin based on analysis of reflected light, and treating the located anatomical features using high-energy light. A labeling agent can be administered to optically differentiate the anatomical feature.

47 Claims, 3 Drawing Sheets

(51) Int. Cl.
  *A61B 18/00* (2006.01)
  *A61B 90/00* (2016.01)
  *A61B 5/00* (2006.01)
  *A61B 17/00* (2006.01)

(52) U.S. Cl.
  CPC .......... *A61B 5/0071* (2013.01); *A61B 90/361* (2016.02); *A61B 2017/00061* (2013.01); *A61B 2018/00458* (2013.01); *A61B 2018/00476* (2013.01); *A61B 2018/00577* (2013.01); *A61B 2018/00625* (2013.01); *A61B 2018/00642* (2013.01); *A61B 2018/00672* (2013.01); *A61B 2018/00678* (2013.01); *A61B 2018/00702* (2013.01); *A61B 2018/00708* (2013.01); *A61B 2018/00785* (2013.01); *A61B 2018/00904* (2013.01)

(58) Field of Classification Search
  CPC .......... A61B 2018/00708; A61B 2018/00785; A61B 2018/00904; A61B 5/0071; A61B 90/361; A61K 49/001; A61K 49/0021
  See application file for complete search history.

(56) References Cited

U.S. PATENT DOCUMENTS

| | | |
|---|---|---|
| 2003/0072759 A1 | 4/2003 | Schoemaker et al. |
| 2003/0139330 A1 | 7/2003 | Banham et al. |
| 2004/0006328 A1 | 1/2004 | Anderson |
| 2006/0004347 A1* | 1/2006 | Altshuler ............. A61B 18/203 606/4 |
| 2008/0020976 A1 | 1/2008 | Garbe et al. |
| 2009/0299268 A1 | 12/2009 | Anderson |
| 2010/0292680 A1 | 11/2010 | Bragagna et al. |
| 2011/0190745 A1 | 8/2011 | Uebelhoer et al. |
| 2011/0212157 A1 | 9/2011 | Edelson et al. |
| 2013/0084243 A1 | 4/2013 | Goetsch et al. |
| 2013/0338626 A1* | 12/2013 | Ferren ...................... A61K 8/02 604/501 |
| 2014/0074193 A1 | 3/2014 | Luzon et al. |
| 2014/0107635 A1 | 4/2014 | Poran et al. |
| 2015/0032092 A1 | 1/2015 | Adanny |
| 2015/0251016 A1 | 9/2015 | Vo-Dinh et al. |

* cited by examiner

SYSTEMS AND METHODS FOR SELECTIVE TARGETING OF STRUCTURAL FEATURES IN TREATING SKIN CONDITIONS

CROSS-REFERENCE TO RELATED APPLICATIONS

This application represents the U.S. National Stage of International Application No. PCT/US2017/018874, filed Feb. 22, 2017, which claims the benefit of U.S. Application Ser. No. 62/298,227, filed Feb. 22, 2016, and entitled "Novel Method for Treatment of Hyperhidrosis by Labeling Sweat Glands Followed by Selective Targeted Ablation by a Smart Laser," and U.S. Application Ser. No. 62/442,690, filed Jan. 5, 2017, and entitled "Systems and Methods for Selective Targeting of Structural Features in Treating Skin Conditions." The disclosure of each of the above-cited applications, as well as any references cited therein, is hereby incorporated by reference.

FIELD OF THE INVENTION

This document concerns an invention relating generally to locating anatomical features in the skin using a labeling agent to optically differentiate the features, and to the automated delivery of high-energy light to anatomical features located by analyzing light reflected from the skin, useful for such applications as the treatment of hyperhidrosis by the selective ablation of sweat glands via targeted application of coherent light.

BACKGROUND

Sweating (also known as perspiration, diaphoresis, or hidrosis) involves the secretion of fluids by sweat glands in the skin. Sweat glands are found in the palms of the hands, soles of the feet, and underneath the arms (i.e., underarms or "armpits"), also known as the axilla. One of the primary functions of sweating is regulation of body temperature, as evaporation of sweat from the skin has a cooling effect. But sweating can reach excessive levels, and is considered to be abnormally high when it is not necessarily related to increases in body temperature, exercise, or high levels of stress. Excessive sweat may soak through clothing or drip off the skin and could disrupt normal daily activities. Abnormally high sweating can also result in social anxiety and embarrassment.

There are two main types of sweat glands in the skin: eccrine glands and apocrine glands. Eccrine glands, which can be found over the entire body, with the highest density on palms of the hands and soles of the feet, open directly onto the surface of the skin. When body temperature rises, eccrine glands provide thermoregulation by secreting fluid onto the surface of the skin for evaporative cooling. The fluid from eccrine glands is mainly water and salt. Apocrine glands, which are found in the axillae, anogenital region, periumbilical region, nipples, and areolae, release sweat into the hair follicle before opening onto the skin surface. Apocrine sweat glands produce a proteinaceous fluid that is itself odorless, but may become odoriferous once the proteins are ingested by bacteria that are commonly found on the skin. A third type of sweat gland, referred to as the apoeccrine, can be found in the axillae and may play a role in thermoregulation.

Abnormally excessive sweating, which is known as hyperhidrosis and is a common dermatologic complaint, frequently affects palms, soles, and axillae, although other areas of the body may be affected as well. One treatment for hyperhidrosis involves use of (prescription-strength) antiperspirants with aluminum chloride on affected areas, but these only provide short-term relief. Other treatments involve botulinum toxins, such as OnabotulinumtoxinA (commercially known as "Botox"), which is approved for severe primary axillary hyperhidrosis, but such treatments require a large number of painful injections and must be repeated every few months. Another treatment, referred to as the "miraDry" system, is approved for primary axillary hyperhidrosis, but the system suffers from significant co-morbidity, including neuropathy and pain. Further, neither botulinum toxin nor miraDry is approved for treatment of areas outside of the axillae.

SUMMARY

The present disclosure provides exemplary systems and methods for locating anatomical features in the skin based on an analysis of light reflected from an area to be treated, and applying a high-energy light beam (using, e.g., a treatment laser) to a fraction (or all) of the located anatomical features. A labeling agent may be administered to an area of the skin to optically differentiate an anatomical feature of interest from its surroundings. If it does not spontaneously reach the features of interest in an acceptable length of time without external influence, the labeling agent may be induced towards, or otherwise guided to, the anatomical features. The reflected light that is analyzed may result from ambient light, or from light emitted by a floating spot laser or other light source. A camera may be used to capture an image of the area of the skin to be analyzed before treatment, or the reflected spot laser light may be detected using a scanner and analyzed. The treatment laser may be ablative (such as erbium or carbon dioxide lasers) or non-ablative (e.g., some fiber lasers), and may be used to disrupt a targeted anatomical feature. As a non-limiting example, disruption may include thermal ablation of an anatomical structure, promotion of a photoreaction, break down of plasma, damaging of individual cells, vaporization of tissue, and the like. In some configurations, exemplary versions may be applied to treating hyperhidrosis or otherwise targeting glands with a thermally-ablative laser. The foregoing and other aspects and advantages of the invention will appear from the following description. In the description, reference is made to the accompanying drawings which form a part hereof, and in which there is shown by way of illustration one or more preferred embodiments of the invention. Such embodiments do not necessarily represent the full scope of the invention, however, and reference is made therefore to the claims for interpreting the scope of the invention.

DETAILED DESCRIPTION

The following discussion is presented to enable a person skilled in the art to make and use exemplary configurations of the invention. Various modifications to the illustrated configurations will be readily apparent to those skilled in the art, and the generic principles herein can be applied to other configurations and applications without departing from the invention. Thus, configurations of the invention are not intended to be limited to versions shown, but are to be accorded the widest scope consistent with the principles and features disclosed herein. The following detailed description is to be read with reference to the figures. The figures depict selected configurations and are not intended to limit the scope of the invention. Skilled artisans will recognize the examples provided herein have many useful alternatives that fall within the scope of configurations of the invention.

The invention may be described herein in terms of functional and/or logical block components and various processing steps. It should be appreciated that such block components may be realized by any number of hardware, software, and/or firmware components configured to perform the specified functions. For example, different configurations may employ various integrated circuit components, e.g., memory elements, digital signal processing elements, logic elements, diodes, look-up tables, etc., which may carry out a variety of functions under the control of one or more microprocessors or other control devices. Other configurations may employ program code, or code in combination with other circuit components. It should also be appreciated that certain components and functions may be shared and/or shuffled between blocks and among blocks in different versions of the invention, as deemed suitable.

Figure 1:
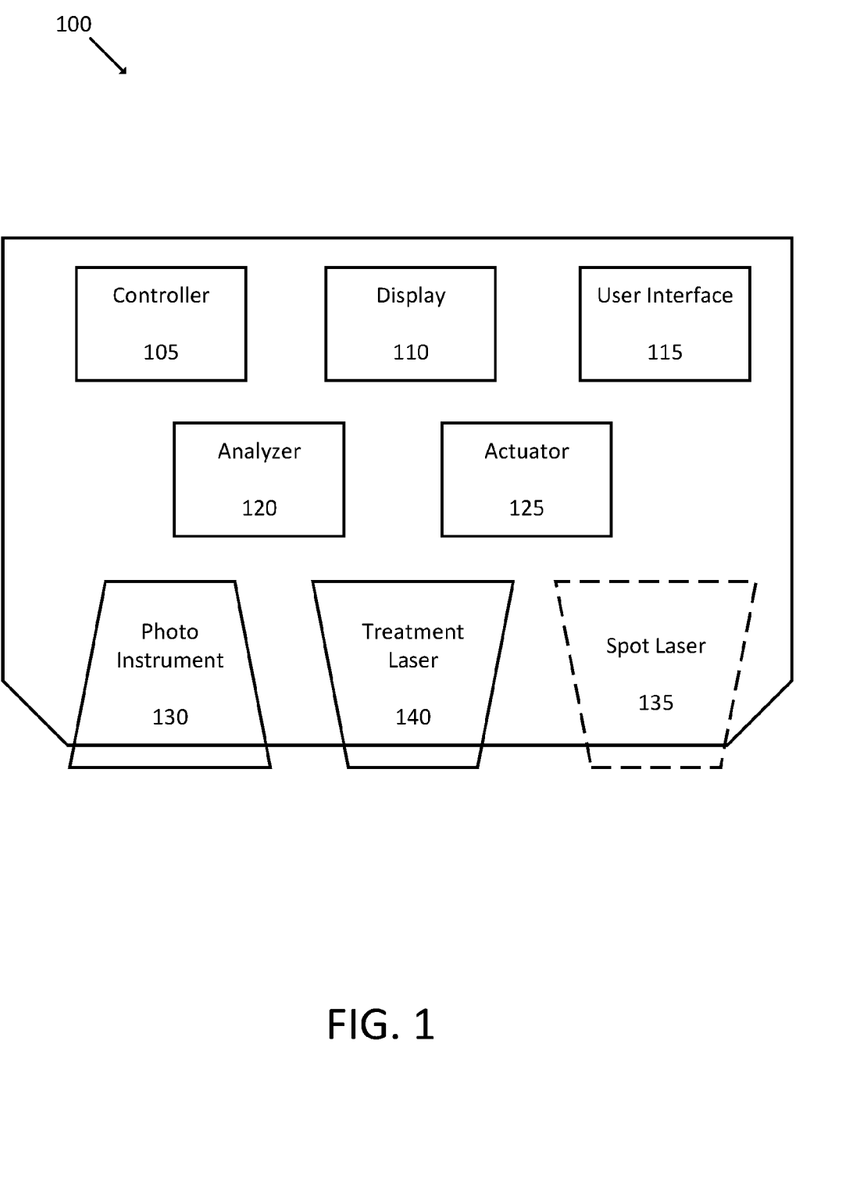
FIG. 1 shows an exemplary system for locating structural features in the skin and applying laser light thereto.

Referring to FIG. 1, an exemplary laser treatment system 100 includes a controller 105 for directing the overall functionality of the system. The controller 105 includes a processor, and memory with instructions (i.e., executable code in the form of software, firmware, etc.) to be executed for controlling the operations of the system 100. A display 110 (which may be a touchscreen) is used to provide prompts, images, etc., and a user interface 115 (which may include a mouse, keyboard, stylus, touchscreen, etc.) is used to receive commands from a user. The system 100 includes a photo instrument 130, which may include one or more of a camera and a scanner with a photosensor, for receiving light reflected off the area of the skin to be treated. In certain configurations, a floating spot laser 135 (or other light source) may be included to emit a light directed at the skin, with its reflection being received at the photo instrument 130. In other configurations, the system 100 may (alternatively or additionally) capture images of the skin (formed using the reflection of ambient light off the skin) with a camera.

Any suitable treatment laser 140 (or other light source) may be used. For example, the treatment laser 140 may emit high-energy light, such as in the infrared range (such as a laser used to emit highly coherent light). An analyzer 120 is used, in a general sense, to analyze attributes of light reflected off the skin. This may include image processing of images captured using a camera, or evaluation of attributes (such as wavelength) of reflected light. An actuator 125 may be used to adjust the position of the spot laser 135 and/or the treatment laser 140. In certain configurations, the two light sources may be immovably secured to each other such that, e.g., they target the same spot on the skin. The actuator 125 may also be used to adjust the position of the photo instrument 130. It is noted that the actuator may be any mechanism that is able to move one or more components of system 100 in various ways, powered electrically or otherwise, using, e.g., motors, magnetic manipulation, etc.

In certain configurations, a light source for detection (such as spot laser 135) and a light source for treating (such as treatment laser 140) may be "co-registered" or "co-axial" so that the detection light source (and associated reflected light from the skin) can be used to detect a target, and the treating light source can be (immediately) triggered to fire at the same location. Reducing the delay between the time the reflected light from the spot laser 135 is received at the photo instrument 130, and the time the treatment laser 140 is fired at the target, reduces the likelihood that, for example, a subject will move the body part being treated, or the target is otherwise relocated.

In alternative configurations, the detection light source can be actuated/aimed independently from the treatment light source (or the two light sources can otherwise be aimed at different locations fixed relative to each other) to allow the two light sources to have different targets. This can be used, for example, in situations in which it is desirable to allow a spot laser to locate a subsequent target to be treated while the treatment laser is treating a current target, or to allow the spot laser to confirm the "post-treatment" state of an already-treated target to evaluate, for example, whether the treatment laser should subsequently be re-aimed at the previous target for additional treatment. If, in certain configurations, multiple spot lasers are included, one spot laser may reflect light to locate the next target, and another spot laser may reflect light at a treated target to evaluate the target or the results of the treatment, and determine whether results were satisfactory or whether retreatment is warranted.

It is noted that although FIG. 1 shows one of each component (e.g., one actuator 125, one photo instrument 130, one spot laser 135, and one treatment laser 140), there may be two or more of each component. For example, multiple actuators may be provided, each associated with various motions, positions, and light sources. Similarly, multiple spot lasers may be provided to facilitate, for example, simultaneous evaluation of multiple locations. And multiple photo instruments may be included, for example, to receive reflections from different sources. It may be, for example, that identification of targets are more accurate in certain applications if light is directed at a suspected target from multiple angles, and the multiple reflections detected and analyzed to locate features of interest. With one spot laser, light may be emitted at a suspected target from one angle, and the spot laser relocated to emit light at the suspected target from a second angle. This could significantly increase the delay between identification/confirmation of a target (in large part due to the time taken to actuate and re-aim the spot laser), and the application of light from a treatment laser. Having multiple spot lasers could decrease this delay between targeting and treatment. Moreover, multiple treatment lasers may be provided to enable simultaneous treatment of multiple targets. This may be particularly advantageous if the number of targets to be treated is in the thousands, and the overall treatment time is to be reduced.

In some configurations, exemplary versions may be applied to treating hyperhidrosis or otherwise targeting sweat glands with a thermally-ablative laser. The locations of sweat glands in the skin are not readily apparent from observations of the skin with the naked eye. Although they are fairly close together, sweat pores are spaced irregularly throughout the skin. To enhance accurate targeting of the sweat glands, as distinguished from surrounding tissue, sweat glands may be "marked" as targets for ablation. In certain implementations, a labeling agent, such as methylene blue, may be used to stain sweat glands to be targeted using iontophoresis. The target is, for example, the skin pore through which the eccrine sweat gland emits sweat. The methylene blue is selectively "taken up" at the surface of the pore to form a blue dot. Iontophoresis of methylene blue results in "sweat pore patterns" but does not result in the presence of methylene blue throughout the gland. Rather, the methylene blue is limited to the portion of the eccrine sweat gland in the epidermis, otherwise known as the acrosyringium (see also FIG. 3A, discussed below).

A camera, integrated with a laser hand piece, may be used to photograph the pore pattern. Image feature recognition is used to locate the centers of the dots on a grid (e.g. a Cartesian grid) for targeting. The coordinates of these target points are then passed to the computer that controls the treatment laser. The treatment laser is then actuated so that the laser aperture targets desired coordinates. An ablative wavelength (e.g. erbium at 2940 nanometers (nm) or $CO_2$ at 10,600 nm) can then be used to drill a vertical hole through the skin at the desired location at a desired depth. The laser beam will ablate the acrosyringium and a portion of (or all of) the ductal portion of the eccrine apparatus, possibly even extending all the way to the secretory coil. The laser beam will be no wider than 500 microns, and in certain configurations, a narrower beam with a diameter of 75-200 microns may be preferable, so that the ductal portion of the eccrine apparatus (the width of which is 40-80 microns) will be ablated without undesired or excessive damage to surrounding skin. After the initial "hole" is drilled (i.e., once a column of tissue containing the eccrine gland is vaporized), a controller can then automatically target the treatment laser at a second target, and fire the narrow ablative beam to drill a second hole. Alternatively or additionally, labeled sweat glands can be located by emitting light from a floating spot laser, and detecting the reflection of that light. Based on attributes of the reflection (such as wavelength), the positions of the labeled sweat glands can be determined.

Exemplary configurations are well-suited to targeting anatomical features that are microscopic, that do not have pigmentation or other optically-distinguishing features, and/or are very numerous (e.g., in the thousands) such that manual targeting is not practical. The laser light may be used to bring about a desired result, not limited to ablation. For example, the light may be used to initiate, promote, or induce a photochemical reaction (for applications related to, for example, oncology, surgery, tissue engineering, etc.). In yet other configurations, light may be used to, for example, break down plasma, damage or disrupt individual or groups of cells, vaporize tissue, etc. In addition to hyperhidrosis, an ablative approach can be useful for, e.g., targeting sebaceous glands in the treatment of acne, removal of white (or otherwise with little pigment) hair, etc.

Figure 2:
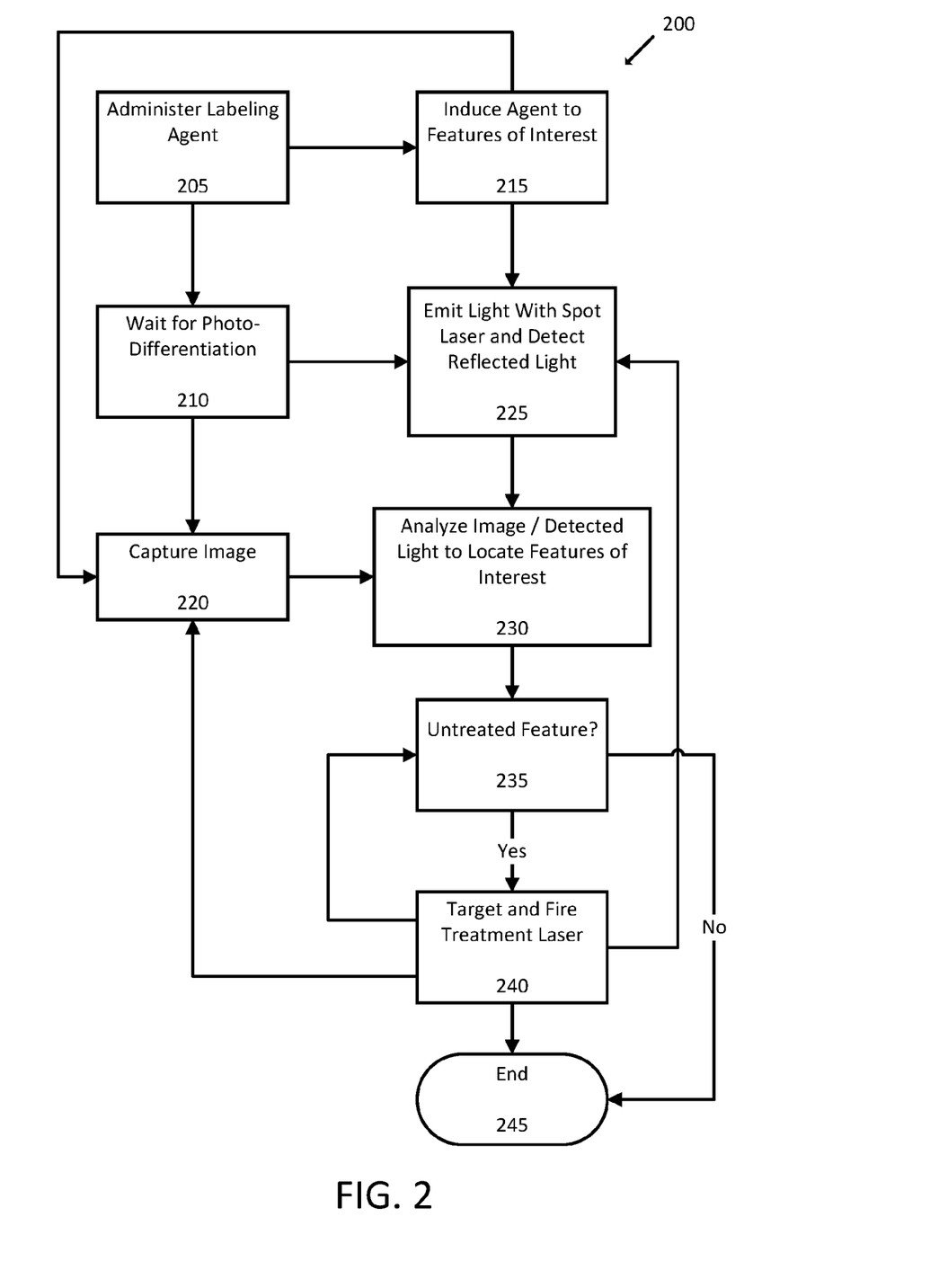
FIG. 2 provides a series of steps involved in an exemplary method for locating structural features of interest and applying a laser light thereto.

Referring to FIG. 2, an exemplary process 200 may begin with administration of a labeling agent (205) to an area of the skin to be treated. The labeling agent is intended to optically distinguish an anatomical feature of interest (such as a sweat gland). A high-contrast (and biologically inactive) dye, such as methylene blue, may be a suitable labeling agent to target, for example, sweat glands in the skin. In other situations, the labeling agent may be, e.g., metallic nanoparticles (such as gold nanoparticles for labeling the orifice of sebaceous glands, which have lipid-rich secretions and are associated with acne), or may be a drug or other chemical which itself may not effectively "label" a targeted feature, but may be metabolized or may react with other chemicals (which may be already present in the skin, or which may also be administered to the skin) to yield a metabolite or chemical product that is able to photo-distinguish the features of interest. For example, administering aminolevulinic acid (ALA) to cells can yield porphyrin with fluorescent properties (in about 30 minutes to 2 hours).

The administered labeling agent may itself reach the targeted feature in a given amount of time (210). In certain situations, the labeling agent may need to be "guided" to the features of interest (at least to reach them in an acceptable amount of time), in which case the labeling agent may be induced to the targeted anatomical features (215). For example, methylene blue, which is a cation (i.e., positively charged), may be guided to sweat glands using iontophoresis (by placing an anode (i.e., positive electrode) on the skin). By applying a low-level electric current, the methylene blue travels to the duct of the eccrine gland, staining part of the gland. For other labeling agents, such as gold nanoparticles, an intense vibration applied via ultrasound may be used to guide the nanoparticles to the anatomical features of interest (which may be effective when the labeling agent, in a sense, needs to "swim upstream" to get to the targets).

The area of the skin being treated may be imaged (220) using a camera, and the image may be analyzed (230) to locate the labeled features. Methylene blue, as one non-limiting example, has a distinct absorption spectrum, absorbing light very well at 670 nm (in the red part of the spectrum) and having a blue appearance. By contrast, melanin in the skin absorbs blue and near infrared light. The system may thus capture wavelengths (1) that are absorbed by both methylene blue and melanin, and (2) that are absorbed by melanin but not by methylene blue, and in image processing, subtract the melanin signal (2) from the combination signal (1) to identify the methylene blue. Methylene blue is advantageous because there are no blue features natively found in the skin. This allows for strong absorption contrast—i.e., high reflectance of skin where eccrine ducts are not, and low reflectance where the ducts are stained with methylene blue, resulting in blue "dots" that have excellent contrast.

An additional processing technique involves thresholding to, for example, minimize shadowing effects (depending on how the skin is illuminated) resulting from such features as wrinkles in the skin. This might use (for example) spectral (i.e., wavelength-dependent) processing if multiple wavelengths are involved, or processing the color channels of an RGB camera—in which case the red (R) channel of pixels will have contrast information for methylene blue, and the blue (B) and green (G) channels will have high-contrast information for melanin but not methylene blue—by, e.g., subtracting (or taking a ratio) of the signals from the different channels. Separating the channels can thus be useful for distinguishing methylene blue (or other labeling agents) from surrounding features. Additionally, a pixel intensity threshold for discriminating dark spots can also help enhance discrimination. This processing can provide a "bitmap" with regions of identified pixels associated with the eccrine duct apparatus.

Spatial filtering can also be used to provide criteria to help target features falling within a certain (expected) range of sizes for the features of interest (approximately 50 microns for eccrine ducts). For example, by requiring a certain minimum number of adjacent pixels, but no more than a maximum number, the system could reduce the number of false positives (i.e., firing a laser at locations without the feature of interest). A spot that is too small (e.g., a single pixel) could be due to, e.g., unintended labeling of a feature that is not being targeted, or to error/noise, and firing a laser at such a spot may thus ablate or treat otherwise normal regions. Similarly, treating a spot that is too big (i.e., beyond the range of expected sizes for the feature of interest, such as 100 microns in the case of eccrine glands) could also apply excessive laser light at surrounding (otherwise normal) areas of the skin.

Alternatively or additionally, a spot laser may be used to emit light at the skin, and the reflected light detected (225) using, e.g., a scanner or other photosensors. The reflected light may then be analyzed (230) in similar fashion by determining attributes (such as wavelengths) of the reflected light. Based on the analysis, it can be determined whether any (untreated) features of interest have been located (235). If so, an optical treatment can be delivered. For example, a laser may deliver high-energy light. Thus, the treatment may be effectuated using a laser aimed (using, e.g., an actuator) at one or more targets at a time (240). The emitted light may be in the infrared range. Once the treatment laser has fired, energy is delivered to the location of the anatomical features to effectuate the treatment, which may include treating, such as disrupting the anatomical features (or a physiological function thereof). As described, treatment may include thermal ablation, promotion of a photoreaction, break down of plasma, damaging of individual cells, vaporization of tissue, and the like. In the described example of the anatomical features being a gland, as a non-limiting example a sweat gland, the treatment may cause the secretion of sweat to be inhibited or reduced. After treatment of a particular spatial location or targeted anatomical feature, the system can determine whether there is another (already-located) untreated feature to be targeted (235) in an available image, and re-aim the laser at the other feature (240). Alternatively, the system can capture another image (220) for analysis (useful in case changes in the skin warrant, for example, re-application with a relatively-lower intensity laser beam), or emit light with the floating spot laser (225) to identify the next anatomical feature to be targeted (if any).

The use of a floating spot laser provides certain advantages, such as enhancing the ability of the system to scale up and down more easily for different fields of view. With an imaging system (which uses a camera to capture an image of the area to be treated), once a feature of interest has been located, the treatment laser is lined up with the relevant pixels in the image. However, because a patient might move after the image is taken but before the treatment laser fires, the laser might "miss" or the system might otherwise make an alignment error. With a floating spot laser that is aligned with a treatment laser, such that both target the same spot, the system can, in a sense, provide more "real time" treatment. That is, the location that is identified as having a label is the same location that is targeted by the treatment laser, and once a feature is suitably targeted, the treatment laser can (virtually simultaneously) be fired at that same location off of which the spot laser light reflected.

On the other hand, an advantage of having an imaging system is the ability to provide an image of the area being treated for review by a healthcare provider. For example, in the process 200 of FIG. 2, before the firing step (240), the system 100 may provide a doctor with the captured image showing a spot that is to be treated on display 110. A Cartesian grid (see FIG. 3B) may be overlaid on the image, or the spot to be treated otherwise indicated on the display (with, e.g., an arrow to the spot, a box/circle around the spot, placing the spot in focus relative to (out-of-focus) surroundings, "graying" out surroundings and/or brightening the spot to be treated relative to its surroundings, etc.). The practitioner may then confirm that treatment should be applied at the indicated spot via user interface 115 (e.g., by touching a confirmation icon on a touchscreen). Moreover, an imaging system approach might be easily adaptable to detection of a relatively greater variety of structural features of the skin.

Figure 3A:
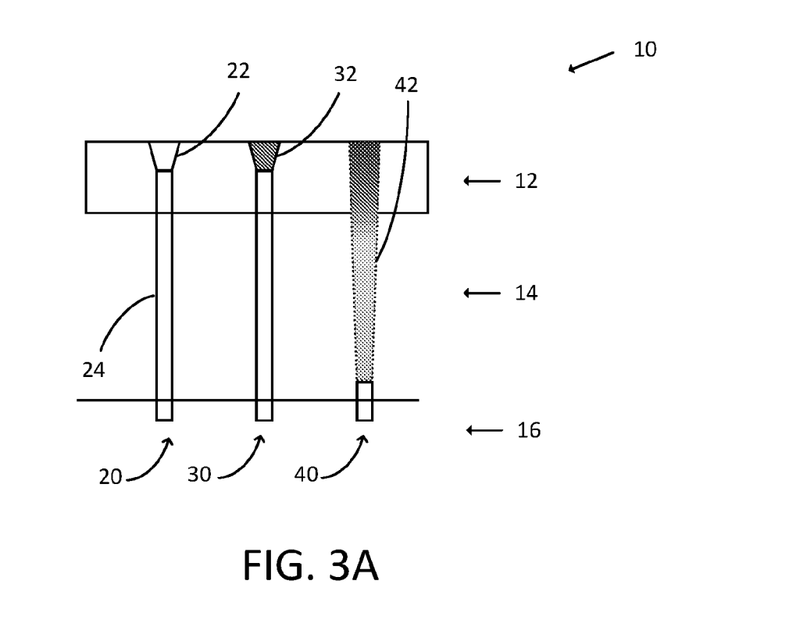
FIG. 3A shows a (not-to-scale) sweat gland as an example of a structural feature that could be located and treated using the exemplary system and method of FIGS. 1 and 2, respectively. After iontophoresis, the blue labeling of the pores is depicted by shading in FIGS. 3A and 3B.
Figure 3B:
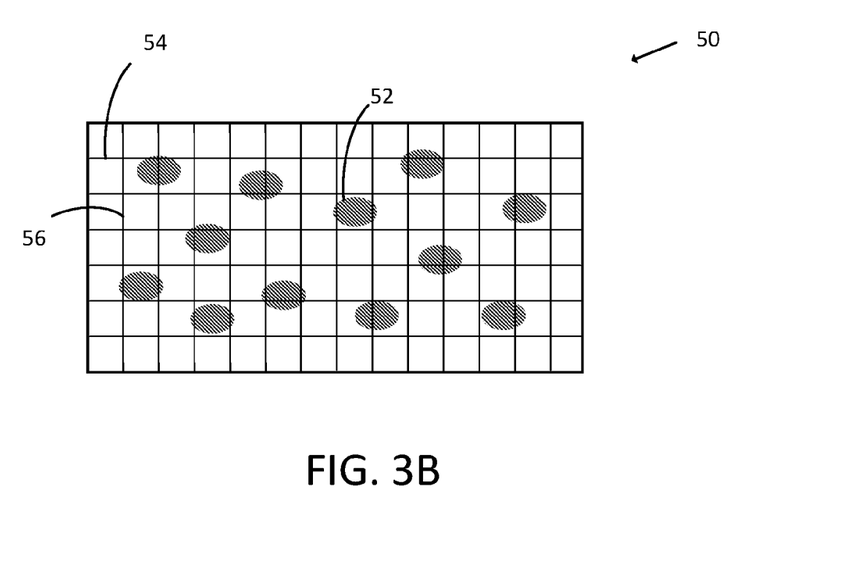
FIG. 3B also shows an exemplary mapping, with x-y coordinates of irregularly spaced blue dots. The coordinates can be passed to an automated controller of a treatment laser system.

Referring to FIG. 3A, an area of the skin 10 is represented with epidermis 12, dermis 14, and subcutaneous fat 16. The skin thickness (epidermis and dermis) can range from 0.5 to 4 millimeters (mm), depending on body site. Three eccrine glands 20, 30, 40 are also illustrated. Gland 20, which is in a pre-labeling state, includes an (un-labeled) acrosyringium 22, a duct 24, and a secretory coil (not shown), which may be in the lower dermis 14 or the subcutaneous fat 16. Gland 30, following the step of labeling or marking (such as by using methylene blue) but prior to treatment, includes a portion of the acrosyringium 32 labeled with methylene blue (as represented by the gray shading). Gland 40, following application of a laser beam, shows an ablated region 42. The depth of ablation, which can be adjusted by varying the type of laser used or the duration or intensity of the laser-light application, is selected so as to cripple or disrupt the eccrine gland. Ablation would encompass the dermal portion of the gland (duct and secretory coil, if located in the lower dermis 14), but ablation depth can also be increased to include a portion of the subcutaneous fat 16 (where the secretory coil may be located). Suitable ablation depths may range from 1 to 4 mm, and can depend on location in the body/skin. FIG. 3B represents an area 50 of the skin to be treated, with (blue) "spots" 52 representing labeled ostia (openings) of the acrosyringium. The system can identify locations of labeled sweat glands according to a Cartesian grid with horizontal lines 54 and vertical lines 56. As shown in FIG. 3B, the x-y coordinates of gland 52 are (x=8, y=3).

The exemplary laser-guided robotics described above is well-suited to supravital targeting of anatomical structures such as glands (e.g., sweat glands), as discussed above, as well as other anatomical structures. For example, even without the introduction of a labeling agent, lipid-selection absorption can be useful to target, for example, sebaceous glands. This is due to the difference in absorption spectra for water and lipids (i.e., 1210 nm versus 1190 nm). The system is particularly advantageous for treating densely-packed or otherwise numerous anatomical structures (with, e.g., hundreds to millions of targets).

Exemplary systems are configured to be highly spatially selective. They may be configured, for example, to disrupt the physiological function of "targets" (cells, tissues, tumors, growths, organs, etc.) to a desired level—such as the secretion of fluids by glands in the skin—without causing any undesired or collateral damage to other anatomical features or to surrounding tissue. To effectuate the disruption permanently or indefinitely—or temporarily if disruption for a duration of time is deemed acceptable, and/or if permanent disruption is deemed harmful or otherwise undesirable—the targeted anatomical features may need to be damaged, destroyed, or vaporized to varying degrees. The parameters of the treatment can thus be set, depending on the characteristics of the particular target and its surroundings, so as to achieve the desired result on (i.e., "treat") only the desired targets with minimal impact on surrounding features. Different anatomical features can be selectively targeted by adjusting, for example, the parameters of the light delivered, such as wavelength, diameter (of the beam), intensity (i.e., power per unit area), type (of light source), etc. If, for example, a lower-powered, narrower beam will effectuate the desired outcome with minimal impact on other tissue, it will generally be desirable over a higher-powered, wider beam.

Other parameters that can be adjusted include duration of treatment. If, for example, a target requires application of a treatment laser for a shorter or longer duration before surrounding tissue is affected, the duration can be adjusted accordingly. In certain situations, it may be more effective to apply multiple instances of light for shorter durations instead of one instance for a relatively longer duration. Similarly, if multiple instances of light are to be applied, depending on the nature of the targeted feature and/or its surroundings, each instance may have the same lower power intensity, and/or the power intensity may be progressively decreased (or increased) after the first instance. Moreover, duration and power intensity can be adjusted up or down between instances as deemed appropriate depending on a re-imaging of a treated location. This can be particularly advantageous when anatomical structures of the same type are expected to significantly vary in resiliency/robustness among different subjects, and even in the same subject depending on location on body and/or natural variability. Consequently, it may be that the first instance is at the (relatively) lowest power intensity and for the shortest duration, and intensity and/or duration are increased only after a re-evaluation of light reflected from a treated spot indicates that a greater intensity will be needed to achieve the desired result.

The effects of each instance of light application on a given anatomical structure may be evaluated by, for example, observing the size, intensity, wavelength, etc., of a labeled spot. For example, if the labeling agent is vaporized proportionally with the target, then an observed reduction in the size of the spot may be positively correlated, or otherwise correspond, with the damage imparted on the structure. Additionally, the labeling agent may be selected such that it changes upon application of the light (through, e.g., photoreaction). The type and degree of change in the labeling agent as a result of the application of light can be correlated with how much treatment reached the intended target (as opposed to surrounding tissue), or with the impact/effect of the light on the anatomical structures. Accordingly, evaluating changes in the characteristics of the (remaining) labeling agent can inform the treatment parameters of subsequent instances of light application.

Moreover, different specific portions of marks/labels can be targeted depending on the structure or the nature of the labeling agent. For example, although the center of a spot will often be the center of the target, and firing at its center may help ensure that most of the impact will be on the structure and not its surroundings, in certain situations, firing at the periphery of a "spot" may have a more desirable outcome depending on, for example, what portion of the anatomical structure is more responsible (relatively) for the physiological function to be disrupted, or depending on what is "beneath" the labeled structure, or on what portion of the structure or its surroundings receives more of the labeling agent. For example, the labeled "spot" may be associated with an adjacent structure, or a periphery or side of the feature of interest, and the center of the spot may not be the center of the targeted feature, requiring an adjustment to the aim of the laser. In certain situations, depending on (for example) the target and the labeling agent used, it may be the case that targeting the structure that is labeled will not be as effective (if at all) as targeting another (unlabeled) location adjacent to the labeled structure (or otherwise a known distance away nearby). That is, it is possible that the labeling agent will be taken up not by the ideal or desired target for bringing about a desired result using the treatment laser, but the optically-differentiated labels may instead "indirectly" mark the locations that should be targeted for receiving laser light.

The present invention has been described in terms of one or more preferred configurations, and it should be appreciated that many equivalents, alternatives, variations, additions, and modifications, aside from those expressly stated, and apart from combining the different features of the foregoing versions in varying ways, can be made and are within the scope of the invention. It should be appreciated that the invention is applicable to other procedures and to achieve other objectives as well. For example, it should be appreciated that the above systems and methods can be implemented using hardware, software, single integrated devices, multiple devices in wired or wireless communication, or any combination thereof. Such changes are not to be construed as describing the only additions and modifications to the invention. It is expressly contemplated that any of the processes or steps described herein may be combined, eliminated, or reordered. Accordingly, this description is meant to be taken only by way of example, and not to otherwise limit the scope of this invention. The patentable scope of the invention is defined by the claims and may include other examples that occur to those skilled in the art.

What is claimed is:

1. A method of targeting anatomical structures in the skin, the method comprising:
   applying a labeling agent to a portion of the skin of a subject to optically differentiate spatial locations that include microscopic anatomical features;
   analyzing light reflected from the skin to locate the anatomical features, each spatial location of each anatomical feature being optically differentiated from surrounding skin as a result of the application of the labeling agent; and
   sequentially targeting a coherent light source at the located anatomical features and delivering coherent light thereto.

2. The method of claim 1 wherein the anatomical features are at least one of glands or hairs.

3. The method of claim 2 wherein the glands are at least one of sebaceous glands or sweat glands.

4. The method of claim 3 wherein the sweat glands are eccrine glands.

5. The method of claim 1 wherein the labeling agent is methylene blue, and wherein the anatomical features are sweat glands.

6. The method of claim 1 further including the step of inducing the labeling agent towards the anatomical feature.

7. The method of claim 6 wherein the labeling agent is electrically charged, and wherein the labeling agent is induced towards the anatomical features by application of an electric field.

8. The method of claim 7 wherein the electric field is applied via iontophoresis.

9. The method of claim 6 wherein the labeling agent is induced towards the anatomical features using vibration administered ultrasonically.

10. The method of claim 9 wherein the labeling agent is a metallic nanoparticle.

11. The method of claim 1 wherein the labeling agent is biologically active.

12. The method of claim 11 wherein the labeling agent is aminolevulinic acid.

13. The method of claim 1 wherein light reflected from the skin is used to form an image of the skin using an imaging device, and wherein the image is analyzed to locate the anatomical features.

14. The method of claim 1 wherein the step of analyzing comprises at least one of detection of an absorption spectrum of the labeling agent, comparison of an attribute of the light reflected from the skin with a threshold, or comparison of sizes of located anatomical features with a range of expected sizes for the anatomical features, wherein the coherent light is delivered only to anatomical features with sizes falling within the range.

15. A system for targeting anatomical features in the skin, the system comprising:
a photo instrument configured to receive light reflected from an area of the skin of a subject;
a coherent light source configured to emit coherent light at targeted anatomical features in the skin;
an actuator configured to select anatomical features in the skin targeted by the coherent light source; and
a controller having a processor and a memory with instructions executable by the processor, the controller being configured to:
analyze light reflected from the skin and received by the photo instrument to spatially locate the anatomical features in the skin, each anatomical feature being optically differentiated from its surroundings as a result of the application of the labeling agent to the skin; and
administer coherent light to multiple sets of anatomical features by using the actuator to sequentially target the coherent light source at spatial locations of each of the located anatomical features without targeting surrounding skin.

16. The system of claim 15 wherein the anatomical feature is located by identifying a location of a label based on one or more optical characteristics, wherein the label marks the location of the anatomical feature in the skin.

17. The system of claim 15 wherein surrounding tissue is avoided by adjusting one or more parameters of the delivery of the coherent light.

18. The system of claim 17 wherein the parameter adjusted is at least one of the duration of coherent light delivery, the number of instances of coherent light delivery, the intensity of coherent light delivered, the precise location targeted relative to the label, or the portion of the label that is targeted.

19. The system of claim 18 wherein the portion of the label that is targeted is a peripheral region of the label.

20. The system of claim 15 wherein the photo instrument is a camera, and wherein the controller is configured to: a. acquire an image of an area of the skin using the camera; and b. process the image to locate the anatomical features targeted by the coherent light source.

21. The system of claim 15 wherein the controller is configured to map relative positions of the anatomical features on a grid overlaid on an area of the skin.

22. The system of claim 15 wherein the anatomical features are at least one of sweat glands, hairs, or sebaceous glands.

23. The system of claim 15 wherein the controller is further configured such that analyzing comprises comparison of an attribute of the light reflected from the skin with a threshold, and wherein anatomical features are located based on the comparison.

24. The system of claim 23 wherein the attribute is intensity of the reflected light, or wavelengths of the reflected light.

25. The system of claim 15 wherein the controller is further configured such that analyzing comprises comparing sizes of located anatomical features with a range of expected sizes for the anatomical features, and wherein the controller is configured to only deliver coherent light to anatomical features with sizes falling within the range.

26. A method of treating hyperhidrosis comprising:
labeling a sweat gland by applying a labeling agent to a portion of the skin;
imaging the portion of the skin to locate the labeled sweat gland; and
delivering energy to the labeled and located sweat gland using a laser, wherein the delivery of energy is sufficient to reduce or eliminate secretions from the labeled sweat gland.

27. The method of claim 26 wherein labeling the sweat gland includes at least one of application of an electric current, or iontophoresis of the labeling agent.

28. The method of claim 26 wherein the labeling agent is methylene blue.

29. The method of claim 26 wherein the labeled sweat gland is identified via image processing for location of the labeling agent.

30. The method of claim 26 wherein the laser has an ablative wavelength.

31. The method of claim 26 wherein the laser is an erbium laser.

32. The method of claim 31 wherein the erbium laser has a wavelength of substantially 2940 nm.

33. The method of claim 31 wherein the laser is a $CO_2$ laser.

34. The method of claim 26 further including the steps of: a. locating a second sweat gland; and b. firing the laser at the second sweat gland.

35. A method for non-invasively treating hyperhidrosis comprising:
imaging a section of the skin to locate a sweat gland; and
ablating the located sweat gland using a laser fired from above the skin.

36. The method of claim 35 further including the step of labeling the sweat gland with a labeling agent.

37. The method of claim 36 wherein the sweat gland is labeled via application of an electric current.

38. The method of claim 36 wherein labeling the sweat gland includes iontophoresis of methylene blue.

39. A system for treating hyperhidrosis including:
a laser;
an imager; and
a controller having a processor configured to execute instructions to:
1) capture an image of a portion of a skin using the imager;
2) process the image to locate a labeled sweat gland from tissue surrounding the sweat gland; and
3) fire the laser at the located sweat gland to disrupt the sweat gland without disrupting the tissue surrounding the sweat gland.

40. The system of claim 39 wherein disruption to tissue surrounding the sweat gland is avoided by adjusting one or more parameters of the delivery of the coherent light.

41. The system of claim 40 wherein the parameter adjusted is the duration of coherent light delivery.

42. The system of claim 40 wherein the parameter adjusted is the number of instances of coherent light delivery.

43. The system of claim 40 wherein the parameter adjusted is the intensity of coherent light delivered.

44. The system of claim 40 wherein the parameter adjusted is the precise location at which the laser is fired relative to the label.

45. The system of claim 39 wherein the laser is aimable under the control of the controller, wherein the processor is further configured to: a. locate a second sweat gland; b. position the laser so as to target the second sweat gland; and c. fire the laser at the second sweat gland.

46. The system of claim 45 wherein the processor is further configured to repeat the locate, position, and fire steps until no additional sweat gland is located.

47. The system of claim 39 wherein the processor is further configured to repeat the locate, position, and fire steps until a predetermined fraction of sweat glands has been treated.

* * * * *